United States Patent
Ilsley

(10) Patent No.: US 7,205,128 B2
(45) Date of Patent: Apr. 17, 2007

(54) METHOD FOR SYNTHESIS OF THE SECOND STRAND OF CDNA

(75) Inventor: Dian D. Ilsley, San Jose, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

(21) Appl. No.: 10/222,368

(22) Filed: Aug. 16, 2002

(65) Prior Publication Data

US 2004/0033499 A1 Feb. 19, 2004

(51) Int. Cl.
*C12P 19/34* (2006.01)
(52) U.S. Cl. .................................. 435/91.1
(58) Field of Classification Search ............... 435/6, 435/91.21; 536/22.1, 24.33, 23.33; 530/350
See application file for complete search history.

(56) References Cited

U.S. PATENT DOCUMENTS

| 5,597,713 | A | | 1/1997 | Kato et al. |
| 5,962,272 | A | | 10/1999 | Chenchik et al. |
| 6,096,499 | A | | 8/2000 | Kozlowski et al. |
| 6,132,997 | A | | 10/2000 | Shannon |
| 6,143,528 | A | | 11/2000 | Hayashizaki |
| 6,326,175 | B1 | | 12/2001 | Guegler et al. |
| 6,582,906 | B1 | * | 6/2003 | Cao et al. ............... 435/6 |
| 2004/0014072 | A1 | * | 1/2004 | Ishino et al. ............ 635/6 |

OTHER PUBLICATIONS

Gubler et al. A simple and very efficient method for generating cDNA libraries. Gene, vol. 25, pp. 263-269, 1983.*
Harrington et al. Initiation of RNA-primed DNA synthesis in vitro by DNA polymerase alpha-primase. Nucleic Acids Res., vol. 23(6), pp. 1003-1009, 1995.*
Holmes, AM et al. Initiation of DNA synthesis by the calf thymus DNA polymerase-primase complex. J Biol Chem., vol. 260, No. 19, pp. 10840-10846, 1985.*
Arezi et al. Eukaryotic DNA primase. TIBS, vol. 25, p. 572-576, Nov. 2000.*
Hubscher et al. Eukaryotic DNA polymerases, a growing family. TIBS, vol. 25, p. 143-147, Mar. 2000.*
Alessio et al. Second-strand cDNA synthesis with *E.coli* DNA polymerase I and RNase H: the fate ofinformation at the mRNA 5' terminus and the effect of *E.coli* DNA ligase. Nucleci Acids Res., vol. 16, No. 5, pp. 19992014, 1988.*
Harrington et al. Initiation of RNA-primed DNA synthesis in vitro by DNA polymerase alpha-primase. Nucleic Acids Res., vol. 23, No. 6, pp. 1003-1009, 1993.*
Eberwine J., "Amplifications of mRNA Populations Using a RNA Generated from Immobilized Oligo(dT)-T7 Primed cDNA", *Biotechniques* (1996), 20:584-591.
Eberwine J. et al., Analysis of Gene Expression in Single Live Neurons, *PNAS USA* (1992), 89:3010-3014.
Gronostajski R. et al., "Purification of a Primase Activity Associated with DNA Polymerase α from HeLA Cells", *The Journal of Biological Chemistry* (1984), 259: 9479-9486.
Ilsely D. et al., "Acyclic Guanosine Analogs Inhibit DNA Polymerases α, δ, ε With Very Different Potencies and Have Unique Mechanisms of Action", *Biochemistry* (1995), 34:2504-2510.
Johnson, K., "Conformational Coupling in DNA Polymerase Fidelity", *Annu. Rev. Biochem* (1993), 62:685-713.

(Continued)

*Primary Examiner*—Kenneth R. Horlick

(57) ABSTRACT

Synthesis of the second strand of cDNA using pol α-primase is provided. Pol α-primase is used to initiate primers on a cDNA strand de novo, followed by extension of the primer with pol α-primase, a second DNA polymerase or a combination thereof. In a preferred embodiment, pol α-primase extends the primer, followed by addition of a second DNA polymerase, preferably Klenow fragment.

12 Claims, 1 Drawing Sheet

OTHER PUBLICATIONS

Kirk B. et al., "Eucaryotic DNA Primase Does Not Prefer To Synthesize Primers at Pyrimidine Rich DNA Sequences When Nucleoside Triphosphates Are Present at Concentrations Found in Whole Cells", *Biochemistry* (1997), 36:6725-6731.

Lodish et al., "Eukaryotic Proteins that Replicate SV40 DNA in Vitro Exhibit Similarities and Differences with *E. Coli* Replication Proteins", *Molecular Cell Biology*, 3rd ed., p. 378-380.

Phillips J. and Eberwine J., "Antisense RNA Amplification: A Linear Amplification Method for Analyzing the mRNA Population from Single Living Cells", *Methods: A Companion to Methods in Enzymology*, (1996), 10:283-288.

Sambrook et al., Molecular Cloning: A Laboratory Manual, Second Edition, Cold Spring Harbor Laboratory Press (1989)—Table of Contents.

Stillman, B., "Initiation of Eukaryotic DNA Replication in Vitro", *Ann. Rev. Cell Biol.* (1989), 5:197-244.

Thompson H. et al., "Arabinofuranosyl Nucleotides Are Not chain-Terminators during Initiation of New Strands of DNA by DNA Polymerase α-Primase", *Biochemistry* (1995), 34 11198-11203.

Van Gelder R. et al., "Amplified RNA Synthesized from Limited Quantities of Heterogeneous cDNA", *PNAS USA* (1990), 87:1663-1667.

Waga, S. and Stillman, B., "Anatomy of a DNA Replication Fork Revealed by Reconstitution of SV40 DNA Replication in Vitro", *Nature* (1994), 369:207-212.

\* cited by examiner

METHOD FOR SYNTHESIS OF THE SECOND STRAND OF CDNA

FIELD OF THE INVENTION

The present invention relates to the field of nucleic acid synthesis, more particularly the synthesis of a double-stranded cDNA from mRNA ("RNA").

BACKGROUND OF THE INVENTION

Standard protocols exist in the literature for generating double-stranded cDNAs from cellular mRNA. See, e.g., Sambrook, Fritsch, and Maniatis, *Molecular Cloning: A Laboratory Manual*, Second Edition, Cold Spring Harbor Laboratory Press, 1989.

Generally, to prepare a double stranded cDNA from RNA, a first cDNA strand is synthesized using RNA as a template, resulting in an mRNA:DNA hybrid. The mRNA is then degraded by enzymes such as RNAse H. The second cDNA strand is then synthesized by using the first cDNA strand as a template.

Many methods exist for the synthesis of the second strand, but these methods have disadvantages. One method involves self-priming. The 3' termini of single-stranded cDNAs form hairpin structures that can be used to prime synthesis. In this method, the RNA strand of the hybrid is degraded, and the resulting hairpin loop that forms is utilized as a primer by Klenow fragment or RT to initiate synthesis of the second strand. The loop is then digested with the single-stranded-specific nuclease S1 to yield a double-stranded cDNA. A self-primed synthesis of the second strand is a poorly controlled reaction, and the subsequent cleavage of the hairpin structure can lead to the loss or rearrangement of sequences corresponding to the 5' terminus of the mRNA.

Another method involves nick translation. RNAase H produces nicks and gaps in the RNA strand of the hybrid, creating a series of RNA primers that can be extended by *E.coli* DNA polymerase I. With nick-translation, the amount of RNAase H activity must be closely monitored and controlled; there must be sufficient hydrolysis of the RNA to generate large gaps, but too much degradation will result in few or no primers for synthesis. The length of the RNA primers is also important in terms of the melting temperature (Tm), and forming a stable complex between the primer and the DNA template. Further, the existence of a series of DNA fragments representing the second strand must be ligated to generate a full length second strand. The ligation reaction is often inefficient, especially when a gap exists between the two DNA fragments.

Another method employs primed synthesis using random primers or homopolymeric tailing. In random priming, random hexamers serve as primers for DNA synthesis by T4 DNA polymerase. This method requires the addition of T4 ligase and T4 polynucleotide kinase for ligation of the fragments to generate a continuous second strand. A problem with random hexamer priming is that the reaction is performed at 37° C., which is above the Tm for annealing of the hexamers to the DNA template. In addition, a strong sequence influence exists; GC-rich regions are primed at a higher frequency than AT-rich regions. In areas of the template where there is secondary structure, the hexamers may not anneal. Hence, secondary structure can have a strong influence as to where synthesis is initiated and terminated, which can result in an incomplete synthesis of the second strand. Furthermore, random priming requires the synthesis of the random primers on a DNA synthesizer followed by exogenous annealing, which can be burdensome.

In another method terminal transferase is used to add homopolymeric tails of dC residues to free 3'-hydroxyl groups in the first DNA strand. This tail is then hybridized to oligo(dG), which serves as a primer for the synthesis of the second strand. A problem with homopolymeric tailing by terminal transferase is that the reaction can not be closely controlled. The length of tails added can vary significantly as well as the number of RNA strands that get tailed. In addition, oligo(dG) and oligo(dG):poly(dC) can form stable secondary structures that can inhibit synthesis by "tying up" the primer in secondary structure and thus inhibiting its ability to prime synthesis.

Thus, there remains a need for a reliable method for preparing the second strand of cDNA.

SUMMARY OF THE INVENTION

In one aspect, the present invention provides a method for preparing double stranded cDNA comprising synthesizing a first cDNA strand using an RNA strand as a template to obtain a cDNA:RNA hybrid, separating the first cDNA strand from the RNA strand, contacting a pol α-primase with the first cDNA strand, wherein the pol α-primase synthesizes an RNA primer using the first cDNA strand as a template and extending the RNA primer with pol α-primase, a second DNA polymerase or a combination thereof by using the first cDNA strand as a template to generate a double stranded cDNA.

In another aspect, the present invention provides a process for preparing a double stranded cDNA comprising the steps of separating an RNA strand from a cDNA strand of a double stranded cDNA:RNA hybrid, contacting a pol α-primase with the separated cDNA strand, wherein the pol α-primase synthesizes an RNA primer using the first cDNA strand as a template and extending with pol α-primase, a second DNA polymerase or a combination thereof the RNA primer using the cDNA strand as a template to generate a double stranded cDNA.

In another aspect, the present invention provides a process for preparing a double stranded cDNA comprising synthesizing a primer with pol α-primase on a cDNA strand followed by primer extension with the pol α-primase, a second DNA polymerase, or a combination thereof, to obtain a double stranded cDNA.

A preferred method of extending the primer is by having pol α-primase extend the primer initially followed by addition of a second DNA polymerase with high processivity. A preferred second DNA polymerase is Klenow fragment.

DETAILED DESCRIPTION OF THE INVENTION

Figure 1:
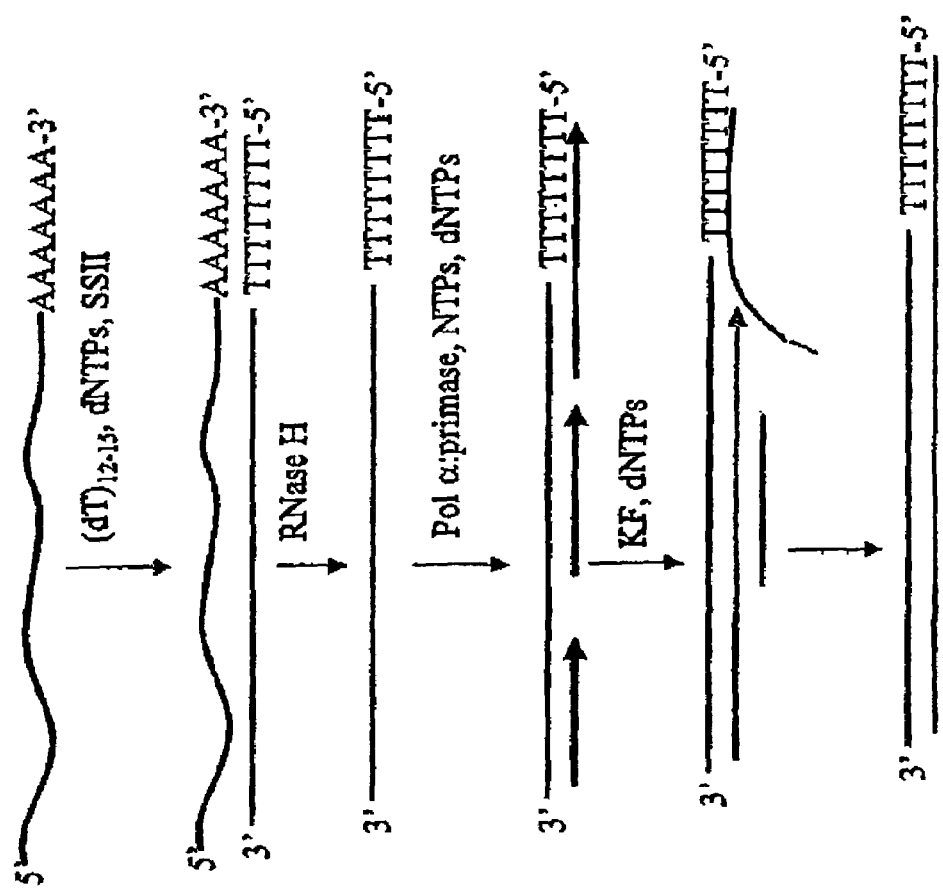
FIG. 1 illustrates synthesis of double stranded cDNA from a single strand of mRNA. The first cDNA strand is synthesized using a reverse tranrcriptase and an oligo(dT) primer. The RNA strand is then digested. Pol α-primase is then added, which initiates de novo synthesis of RNA primers randomly along the cDNA template and then converts them substantially to DNA primers. Klenow fragment is then added to complete the synthesis of the second cDNA strand, by extending the primer (RNA-DNA fragment) closest to the 3' end of the first cDNA strand, and displacing all downstream primers.

The present invention provides a method of synthesizing double stranded cDNA using pol ∝-primase. Pol ∝-primase is disclosed in U.S. Pat. No. 6,096,499 ("Kozlowski et al.").

To prepare a double stranded cDNA from mRNA, one cDNA strand is first synthesized using the mRNA as a template. The first strand can be transcribed using methods well known in the art. See U.S. Pat. No. 5,962,272 (Chenchik et al.). Generally, a reaction mixture containing mRNA, deoxy-nucleoside triphosphates (dNTPs) and a DNA polymerase having reverse transcriptase activity is used.

The first strand can be synthesized, for example, with reverse transcriptase or any other DNA polymerase having reverse transcriptase activity. Non-limiting examples of such polymerases include inter alia those derived from organisms such as thermophilic and archaeobacteria, retroviruses, yeast, *Neurospora, Drosophila*, primates and rodent (See Chenchik at al.). Specific examples of such polymerases include inter alia the DNA polymerase of Moloney murine leukimia virus (M-MLV) (See U.S. Pat. No. 4,493,531), and M-MLV reverse transcriptase lacking RNAse H activity (See U.S. Pat. No. 5,405,776). Other examples include those from Avian Myelobla Stosis Virus (AMV) and Human Immunodeficiency Virus (HIV). DNA polymerases possessing reverse transcriptase activity can readily be purchased commercially. Examples of commercial polymerases with reverse transcriptase activity include SUPERSCRIPT II, which can be purchased from INVITROGEN (Carlsbad, Calif.), and OMNISCRIPT, which can be purchased from QIAGEN (Valencia, Calif.).

DNA polymerases, including reverse transcriptase, need a primer to start synthesis. Preferably, an oligo(dT) primer is annealed to the poly A tail of the RNA strand. The oligo(dT) primer is most preferably a short single stranded oligonucleotide of 12–18 nucleotides. In other embodiments, the oligonucleotide can be a double stranded primer, including a vector primer, having a single stranded portion with oligo(dT) sequence (See Chenchik et al.).

The enzyme having reverse transcriptase activity is then added to the RNA template in the presence of a primer, preferably oligo(dT). An adequate amount of nucleotides (dATP; dCTP; dGTP and dTTP) are added to the reaction mixture, preferably in a buffer. The buffer can contain various ions such as magnesium ions.

The reverse transcriptase then extends the primer, resulting in a DNA:RNA hybrid. Kits such as CELLS-TO-CDNA from AMBION (Austin, Tex.), FIRST STRAND CDNA SYNTHESIS from AMERSHAM BIOSCIENCES (Piscataway, N.J.) and SMART PCR CDNA SYNTHESIS from BD BIOSCIENCES CLONTECH (Palo Alto, Calif.) can be used for synthesizing the first cDNA strand in a facile manner. One of skill in the art would appreciate that the present invention is not limited by the method of synthesis used to prepare the first cDNA strand.

Transcription of the first strand results in a DNA:RNA hybrid. The DNA strand can be separated from the RNA strand of the hybrid by methods well known in the art. See e.g. U.S. Pat. No. 5,728,526 ("George, Jr. et al."). One approach to separating the strands is by digestion of the RNA strand. An RNAse such as RNAse H can be used to digest the RNA strand of the hybrid, thus resulting in a single stranded DNA. Another approach for separating the DNA strand from the RNA strand is by denaturation of the hybrid. The hybrid can be denatured by raising the temperature, lowering the ion concentration or using an agent that disrupts hydrogen bonds, such as urea and formamide. To denature with heat, the temperature is preferably raised to from about 75° C. to about 110° C. The two strands can also be separated enzymatically, such as by using a helicase. When separating the strands by other than digestion, a subsequent separation step may be necessary to further separate the denatured single stranded RNA from the denatured single stranded DNA. In a preferred embodiment, the single strand is purified by crystallization out of a suitable solvent, such as ethanol.

After separation and preferably purification, a "first" cDNA strand is obtained. The first cDNA strand is then used as a template by pol ∝-primase for the synthesis of a second cDNA strand. Generally, a reaction mixture comprising the first cDNA strand, pol ∝-primase, dNTPs and NTPs is incubated to allow for synthesis of the second strand, with optional addition of another DNA polymerase.

Pol ∝-primase is a eukaryotic DNA polymerase capable of binding single-stranded DNA and initiating DNA synthesis de novo. Pol ∝-primase is a four-subunit complex (49, 58, 68 and 180 KD) that contains two enzymatic activities: DNA primase and polymerase. The larger subunits, 180 and 68, are responsible for polymerase activity while the smaller subunits, 49 and 58, are responsible for the primase activity.

The subunits of DNA primase have been cloned as cDNA from both mouse and human, and their sequences are reported in EMBL/GenBank computer-accessible public databases, among others. See Kozlowski et al. Additionally, the synthesis of oligonucleotides by the subunits of pol ∝-primase have been studied in the art. For example, one study measures the inhibition of the polymerase activity of pol ∝-primase with acyclic nucleotide analogs, such as acyclovir, canciclovir and penciclovir. Ilsely et al., *Biochemistry* 1995, 34, 2504–10. Kozlowski et al. discloses methods for identifying modulators and modifiers of the primase unit of pol ∝-primase.

Without being bound by any theory, pol ∝-primase is thought to synthesize the lagging strand during DNA replication in vivo. Lodish et al., *Molecular Cell Biology*, $3^{rd}$ ed., p. 379. The primase activity systhesizes short oligonucleotides, about 7–10 nucleotides in length, during initiation of DNA replication and elongation of the lagging strand. DNA polymerase ∝ then elongates the RNA primer to complete the synthesis of Okazaki fragments. Stillman, B., *Ann. Rev. Cell Biol.* 5:197 (1989). Okazaki fragments are then extended by pol δ and ε, allowing DNA pol ∝ primase to recycle and initiate another Okazaki fragment on the lagging strand. Waga, S. and Stillman, B., *Nature* 369:207 (1994). A unique property of DNA primase is the ability to synthesize oligonucleotides de novo on a template by the formation of an initial dinucleotide. DNA primase initiates synthesis with a triphosphate moiety at the 5' end. Gronostajski et al., *J. Biol. Chem.* 259: 9479 (1984).

According to the current model, pol ∝-primase first binds the DNA template, and then slides along the single-stranded DNA a short distance until it has bound two NTPs. At this point, the enzyme becomes immobilized on the template and becomes poised to begin synthesis of an RNA primer. Unlike prokaryotic DNA primases that show preferences for specific sequences for initiation, eukaryotic primase initiates synthesis at many different sequences. See Kirk et al., *Biochemistry*, 36:6725–6731, 1997.

Initiation by pol ∝-primase is sequence independent, and exogenous primers are not necessary. See Kirk et al. As long as the concentration of NTPs is similar to those found in vivo, the enzyme will initiate randomly all along the template (at low concentrations, the enzyme prefers pyrimidine rich regions). The concentration of NTPs used is preferably in the 1 millimolar range. See id.

On single-stranded DNA, primase synthesizes short RNA oligomers of approximately 7–10 nucleotides in length. Once a primer is synthesized, it is transferred intramolecularly to the polymerase active site.

During the transfer of the primer to the polymerase site, the enzyme complex remains bound to the primer-template. The lack of dissociation from the primer-template renders the primer annealed to the template despite its short length. The association of the enzyme to the primer-template makes the Tm of the primer-template less relevant. The primer-template hybrid, which has a relatively low Tm and dissociates rapidly, becomes stable at higher temperatures and lower ion concentrations. The dissociation of the enzyme from the hybrid becomes a new rate-limiting step.

The secondary structure of the template is reduced as the enzyme slides along the single-stranded template. The reduction in secondary structure may further increase the stability of the primer-template complex.

One of skill in the art would appreciate that pol $\alpha$-primase obtained from many different eukaryotic organism may be used in the present invention. The pol $\alpha$-primase can be from a mammal such as a human or a mouse. Preferably, pol $\alpha$-primase from calf thymus is used. See Thompson et al., *Biochemistry* 34, 11198–11203 (1995). The synthesis of the second strand with pol $\alpha$-primase can be carried out by incubating a buffered reaction mixture containing single standed cDNA, pol $\alpha$-primase, NTPs and dNTPs. The reaction is preferably carried out at a temperature of about 37° C., with a buffer, such as Tris containing various ions, at a pH of about 7.5. EDTA or formamide can be used to stop the reaction when desired. See Ilsely et al., *Biochemistry*, 34, 2504–10, 1995.

The processivity of pol $\alpha$-primase, at about 50–200 nucleotides, is low. Hence, in the absence of another polymerase, pol $\alpha$-primase may be used mainly to synthesize short DNA strands. When longer DNA strands are involved, a second DNA polymerase may be added to further extend the primer. Depending on the length of the first cDNA strand and the time when the second DNA polymerase is added, the second cDNA strand may be generated by using pol $\alpha$-primase, a subsequently added DNA polymerase or a combination thereof. In either case, the second DNA polymerase uses the primer synthesized by pol $\alpha$-primase, even if pol $\alpha$-primase does not extend the primer.

Preferably, the second DNA polymerase is added after the extension of the primer by pol $\alpha$-primase. The intramolecular transfer of the primer to the polymerase unit of the pol $\alpha$-primase without dissociation allows for the primer to be annealed at all times. In a preferred embodiment, pol $\alpha$-primase synthesizes the primer and extends the primer from about 30 to about 70 nucleotides, followed by the addition of a second DNA polymerase to complete the synthesis of the second strand.

One of skill in the art would appreciate that many DNA polymerases can be used as the second DNA polymerase. Depending on the length of the strand, DNA polymerases with different processivity can be used. Processivity refers to the ability of a DNA polymerase to incorporate nucleotides without dissociating from the template. See U.S. Pat. No. 5,972,603 ("Bedford et al."). Klenow fragment can be used which has an average processivity of about 250 nucleotides (Johnson, K. (1993) Annu. Rev. Biochem 62:685–713). See Bedford et al. T4 and Taq DNA polymerases can also be used. The present invention prefers the use of Klenow fragment.

The processivity of the DNA polymerase used can also be altered for optimal result. George, Jr. et al. discloses that a decrease in salt concentration or an increase in nucleotide concentrations increase processivity.

The DNA polymerases used also preferably has displacement activity. Displacement activity is the ability to displace and remove oligonucleotides annealed to the template. See George, Jr. et al. As synthesis of the cDNA strand approaches the 3' end, the downstream oligonucleotides are displaced. Such displacement activity is desired because pol $\alpha$-primase initiates primers all along the template. Thus, initiations that occur in the middle or near the 5' end of the first cDNA strand can be displaced from the template as the second polymerase elongates primers that were initiated at or near the 3' end of the first strand. Polymerases with high processivity also have high displacement activity. The present invention prefers the use of Klenow fragment over other polymerases with displacement activity, such as Bst, Vent and MMLV.

If the second DNA polymerase added does not have displacement activity, the alternative would be to extend all the primers generated by pol $\alpha$-primase and ligating each segment. The method would be somewhat similar to nick translation.

In a preferred embodiment, Klenow fragment is added as a DNA polymerase in addition to pol $\alpha$ primase to generate a full length second cDNA strand. The Klenow fragment is the polymerase unit of polymerase I. The use of a Klenow fragment lacking exonuclease activity is preferred since exonuclease activity can result in digestion of the ends of the strands and an undesirably shortened cDNA. The lack of exonuclease activity in the Klenow fragment eliminates the need to protect the cDNA strand by capping. A Klenow fragment is also desirable because it possesses displacement activity.

After synthesis of the second strand, the second strand contains the RNA primer of 7–10 oligonucleotides synthesized by pol $\alpha$-primase. In one embodiment, the RNA primer is not removed. In another embodiment, the RNA primer is removed by methods well known in the art. One way to remove the primer is by digestion with an RNA specific enzyme, such as RNase H. Nuclease S1 can then be used to digest the any remaining single stranded cDNA.

The resulting double stranded cDNA can then be purified by methods known in the art, and be used to create a cDNA library. For example, the mRNA from a particular cell, such as B cells from the spleen of an immunized mammal, can be separated by using an oligo(dT) probe. A double stranded cDNA library is then made from the mRNA as described above. Such library can be used for identification of new genes and proteins. For example, a cDNA from the library can be fused to a coat protein of a phage for expression on the surface of a phage, followed by selection.

The Following Examples Further Illustrate the Invention:

EXAMPLE 1

A first cDNA strand of an in vitro T7 transcript (ca. 1000 nucleotides long) containing a 3' polyA tail is generated using 200 U SUPERSCRIPT II (RT), 500 uM dNTPs, 100 pmol oligo(dT)$_{12-18}$, 50 mM Tris-HCl, pH 8.3, 75 mM KCl, 3 mM MgCl$_2$, and 10 mM DTT. The reaction is performed at 40° C. for 60 min., followed by heat inactivation of the RT at 70° C. for 10 min. One unit of RNAse H is added to degrade the RNA portion of the RNA:DNA hybrid. After heat inactivation of the RNase H activity at 70° C. for 10 minutes, the first strand is purified by ethanol precipitation. The second strand is generated by the addition of 2 mM NTPs, 25 uM a-$^{32}$P[dATP], dGTP, dCTP, dTTP, 50 mM Tris-HCl, pH 7.5, 5 mM MgCl$_2$, 0.1 mg/mL BSA, and 2 U pol α:primase. The reaction is incubated at 37° C. for 60 minutes. The reaction is split into two part, and 1 U Klenow fragment is added to one of the fractions to extend all of the products to full length products. The reaction is incubated at 37° C. for 30 minutes. Both reactions are then quenched with the addition of an equal volume of 90% formamide/2×TBE. The products are analyzed using gel electrophoresis (6% acrylamide-6M urea-1×TBE) and phosphorimagery. The expected result is the products synthesized by pol α:primase, which represent only the second strand, would have a size distribution of products ranging from 30–1000 nucleotides, while those synthesized by pol α primase/Klenow fragment, would primarily be around 1000 nucleotides.

EXAMPLE 2

A double-stranded cDNA is generated, followed by T7 amplification. The first strand is generated as described in Example 1, with the only difference being an oligo(dT) primer containing a T7 RNA polymerase promoter sequence. The second strand is synthesized using pol ∝-primase and Klenow fragment, as in Example 1, but only cold dNTPs are used. The generated ds cDNA is then used as a substrate in a T7 amplification reaction, using standard procedures as those described in Van Gelder et al. (1990) PNAS USA 87:1663; Phillips amd Eberwine (1996) Methods: a companion to Methods in Enzymol, 10:283; Eberwine et al. (1992) PNAS USA 89:3010; Eberwine (1996) Biotechniques 20:584; and U.S. Pat. No. 6,132,997. The transcripts are then analyzed by denaturing electrophoresis. The product is primarily 1000 nucleotides in length.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods relating to manipulations of DNA, RNA, and proteins can be obtained from numerous publications, including Sambrook, J. et al., *Molecular Cloning: A Laboratory Manual*, 2$^{nd}$ ed., Cold Spring Harbor Laboratory Press (1989). U.S. Pat. Nos. 6,143,528, 5,962,272 and 5,597,713, directed to synthesis of cDNA, can be consulted in that regard. All references mentioned herein are incorporated by reference in their entirety.

What is claimed is:

1. A method for preparing double stranded cDNA comprising the steps of:
    a) synthesizing a first cDNA strand using an RNA strand as a template to obtain a cDNA:RNA hybrid;
    b) separating and purifying the first cDNA strand from the RNA strand;
    c) contacting the first cDNA strand with pol α-primase, wherein the pol α-primase is at a concentration effective for sequence-independent initiation, and wherein the pol α-primase synthesizes an RNA primer using the first cDNA strand as a template; and
    d) extending the RNA primer from about 30 to about 70 nucleotides with the pol α-primase, followed by addition of a second DNA polymerase to generate a full length double stranded cDNA, using the first cDNA strand as a template.

2. The method of claim 1, wherein the second DNA polymerase is Klenow fragment.

3. A process for preparing a double stranded cDNA comprising the steps of:
    a) separating an RNA strand from a DNA strand of a double stranded cDNA:RNA hybrid to form a single stranded cDNA;
    b) contacting the separated cDNA strand with a pol α-primase, wherein the pol α-primase primase is at a concentration effective for sequence-independent initiation, and wherein the pol α-primase synthesizes an RNA primer using the separated cDNA strand as a template; and
    c) extending the RNA primer from about 30 to about 70 nucleotides with the pol α-primase, followed by addition of a second DNA polymerase to generate a full length double stranded cDNA, using the cDNA as a template.

4. The method of claim 3, wherein the second DNA polymerase is Klenow fragment.

5. A process for preparing a double stranded cDNA comprising synthesizing a primer with pol α-primase on a purified cDNA strand, wherein the pol α-primase is present in a concentration effective for sequence-independent initiation, followed by primer extension from about 30 to about 70 nucleotides with the pol α-primase, followed by further extension with a second DNA polymerase to obtain a full length double stranded cDNA.

6. The method of claim 5, wherein the second DNA polymerase is Klenow fragment.

7. The method of claim 5, wherein the double stranded cDNA is about 1000 nucleotides.

8. The method of claim 1, wherein the double stranded cDNA is about 1000 nucleotides.

9. The method of claim 3, wherein the double stranded cDNA is about 1000 nucleotides.

10. The method of claim 3, wherein the first cDNA strand is separated from the RNA strand by enzymatically degrading the RNA strand.

11. The method of claim 10, wherein the first cDNA strand is purified.

12. A process for preparing a full length double stranded cDNA comprising the steps of:
    a) enzymatically transcribing a first DNA strand from an RNA strand to form a DNA:RNA duplex;
    b) isolating the DNA strand from the RNA strand; and
    c) synthesizing a second DNA strand with pol α-primase in combination with another polymerase using the first DNA strand as a template to form full length double stranded cDNA of about 1000 nucleotides,
    wherein the second DNA strand is synthesized by synthesizing a primer with pol α-primase, followed by primer extension from about 30 to about 70 nucleotides with the pol α-primase, followed by further extension with a second DNA polymerase,
    wherein the pol α-primase is present in a concentration effective for sequence-independent initiation.

* * * * *